United States Patent [19]

Wormald

[11] Patent Number: 4,841,153

[45] Date of Patent: Jun. 20, 1989

[54] COAL ANALYSIS

[75] Inventor: Malcolm R. Wormald, Abingdon, England

[73] Assignee: Cogent Limited, London, England

[21] Appl. No.: 225,623

[22] Filed: Jul. 27, 1988

Related U.S. Application Data

[63] Continuation of Ser. No. 908,720, Sep. 18, 1986, abandoned.

[30] Foreign Application Priority Data

Sep. 18, 1985 [GB] United Kingdom ............... 8523060

[51] Int. Cl.$^4$ .................... G01T 3/06; G01N 23/222
[52] U.S. Cl. ............................. 250/390.04; 250/366; 250/367; 250/369; 250/255; 378/159
[58] Field of Search .......... 250/390 C, 390 D, 390 F, 250/255, 270, 392, 366, 367, 358.1, 369; 376/159

[56] References Cited

U.S. PATENT DOCUMENTS

| | | | |
|---|---|---|---|
| 2,830,184 | 4/1958 | Scherbatskoy | 250/264 |
| 2,881,324 | 4/1959 | Scherbatskoy | 250/264 |
| 2,946,888 | 7/1960 | Scherbatskoy | 250/264 |
| 2,990,474 | 6/1961 | Scherbatskoy | 250/270 |
| 2,996,618 | 8/1961 | Goodman et al. | 250/270 |
| 3,041,454 | 6/1962 | Jones et al. | 250/270 |
| 3,781,556 | 12/1973 | Taylor et al. | 250/302 |
| 4,066,892 | 1/1978 | Givens | 250/270 |
| 4,152,596 | 5/1979 | Marshall, III | 250/358.1 |
| 4,278,882 | 7/1981 | Clayton et al. | 250/255 |
| 4,361,534 | 11/1982 | Borsaru et al. | 250/390 C |

FOREIGN PATENT DOCUMENTS

| | | |
|---|---|---|
| 0024835 | 10/1981 | European Pat. Off. . |
| 908485 | 10/1962 | United Kingdom . |
| 2065876 | 12/1979 | United Kingdom . |

OTHER PUBLICATIONS

*Nuclear Instruments and Methods in Physics Research*, vol. 118, No. 3, Oct., 1981, pp. 619–627, A. G. Hanna, et al., "The Prompt Gamma Neutron Activation Analysis Facility of Murr".
*Nuclear Instruments and Methods in Physics Research*, vol. 220, No. 2,3, Mar. 1984, pp. 363–370, R. M. Lieder, et al. "Design of a Bismuth Germanate Anti-Compton Spectrometer and Its Use in Nuclear Spectroscopy".
*IEEE Transactions on Nuclear Science*, vol. NS-28, No. 2, Apr. 1981, pp. 1700–1702, M. A. Raoof, et al., "Multi-element Neutron Activation Analysis of an Iron Ore".
*Nuclear Instruments and Methods in Physics Research*, vol. 223, No. 2/3, Jun. 1984, pp. 416–419, H. T. Millard, "Compton Suppression Gamma-Counting: The Effect of Count Rate".
*Proc. Am. Nucl. Soc. Top. Mfg. Conf.*, 710402, vol. III, pp. 40–46, (1971), D. R. Parsignault, et al., "A Prompt Gamma-Ray Coal Analysis System".
*Nuclear Instruments and Methods*, 198 (1982), pp. 269–276, T. Kishimoto, et al, "A New High Energy Gamma Radiation Measuring System (HERMES)".
*Nuclear Instruments and Methods in Physics Research*, 222 (1984), pp. 479–495, A. M. Sandorfi, et al., "The New BNL High-Energy Gamma-Ray Spectrometers".

*Primary Examiner*—Carolyn E. Fields
*Attorney, Agent, or Firm*—Larson and Taylor

[57] ABSTRACT

An analysis method and system for analyzing coal or other material causes the material to be bombarded with neutrons from a source, and this generates gamma rays from the material which are detected by a detector. The detector has scintillators which generate light when a gamma ray is detected, the light being detected by photomultipliers. Each gamma ray generates two other gamma rays, which may both be wholly absorbed in one or the other scintillator, or one absorbed in one scintillator and one in the other. By analyzing these events, the spectrum of gamma rays may be obtained, giving the composition of the material. One preferred detector has an array of scintillators and coincident gamma ray detection events in three adjacent scintillators detected by detecting if a primary scintillator detector event is coincident with detection events in the other two scintillators. For each detection event, one of the scintillators is selected as a primary scintillator, and two other scintillators, on opposite sides of the primary scintillator, are selected. The detection event in the selected primary scintillator is compared with the detection events in the two other selected scintillators to determine coincidence. In another embodiment, two gamma detectors of differing properties are used, with each detector having a plurality of scintillators. Coincident events are detected in one detector and anticoincident events in the other.

9 Claims, 3 Drawing Sheets

COAL ANALYSIS

This application is a continuation of application Ser. No. 908,720 filed Sept. 18, 1986, now abandoned.

BACKGROUND OF THE INVENTION

1. FIELD OF THE INVENTION

The present invention relates to a system for analysing material such as coal, ore, or similar substances (hereinafter referred to as "coal", by bombardment of the material with neutrons and the detection of gamma rays emitted. It also relates to a gamma ray detector suitable for (but not exclusively for) use in such a system.

2. DESCRIPTION OF THE PRIOR ART

In recent years systems have been developed which use neutron bombardment of coal to analyse the composition of that coal, and so determine its economic value. The general principle of such a system is that a sample of coal is bombarded with neutrons, and these neutrons interact with atoms in the coal to generate gamma rays whose spectrum depends on the atoms with which the neutrons have interacted. If the energy of each gamma ray emitted from the coal can be detected, then the spectrum can be developed and so the elements within the coal identified. The problem, however, with such systems is that it is difficult to detect accurately the gamma ray energies.

It should be noted at this point that the present invention is concerned with detection of gamma rays emitted very quickly (times less than e.g. $10^{-12}$ s) after the neutron interaction. This is commonly referred to as "prompt" neutron activation analysis, to distinguish it from another form of neutron activation analysis in which the gamma rays investigated are those from $\beta$ decay in which the times involved are very much longer. Neutron activation analysis involving $\beta$ decay is unsuitable because not all elements are activated in this way, so that it is not possible to get an accurate analysis of the contents of the coal. Furthermore, different elements have different $\beta$ decay half lives, and so the activity of each element will change in a different way, making accurate analysis very difficult.

Therefore, the present invention is concerned with prompt analysis as this enables coal to be analysed continuously, for example analysis of coal passing continuously down a conveyor. However, the present invention is also applicable to analysis of bulk coal samples, but again with the intention that results are obtained rapidly.

Before discussing the present invention, it is necessary to understand the different types of gamma ray detectors currently used. The first type is the scintillator detector, consisting of a block of material which generates light when a particle such as an electron moving within it is slowed down. Such detectors are commonly made of sodium iodide, usually doped with thallium, and are referred to as NaI(Tl) scintillators. The use of such scintillators is well known for the detection of gamma rays. When a gamma ray interacts with such a NaI(Tl) scintillator there are two possible reactions depending on the energy of the gamma ray. Firstly, the gamma ray may react with an electron of an atom of the scintillator, knocking that electron out of its position in the lattice. This is known as Compton scattering. As the electron moves within the lattice it is slowed by interactions with other electrons and in doing so, generates light. By detecting the total amount of light generated (using a light detector such as a photomultiplier) it is possible to determine the energy of the electron. If all the energy of the gamma ray is absorbed by the electron, then this gives a measure of the gamma ray energy. However, in some cases, only a part of the gamma ray's energy is transmitted, and a gamma ray of different energy continues to move through the lattice. If this gamma ray then reacts with another electron within the scintillator, then all or part of its energy may be transmitted to that electron, generating more light. Thus, the light output from the scintillator will be directly related to the energy of the gamma ray, provided the gamma ray reacts with one or more electrons so that its energy is totally absorbed within the scintillator. However, in many cases only a part of the gamma ray's energy is transmitted to the electrons, and a part is lost, when a gamma ray emerges from the scintillator. Thus, the light spectrum for a gamma ray of a particular energy will have a peak corresponding to the energy of that gamma ray, but a large background level due to other possible reactions, where not all the energy is absorbed within the scintillator.

The second possible interaction, known as pair production, applies when the gamma ray has an energy of at least 1.022 MeV. Such a gamma ray may interact with a nucleus of an atom of the scintillator to generate an electron-positron pair. The electron of this pair passes through the scintillator, and loses energy as light radiation which may again be detected by a photomultiplier. The positron, on the other hand, will react with the first electron it encounters, and they mutually annihilate to generate a pair of gamma rays each having an energy of 511 keV, the two gamma rays travelling in opposite directions. These two gamma rays may then react with electrons in the scintillator by Compton scattering, knocking the electrons out of position and causing them to generate light in the way described above, or may pass directly out of the scintillator. Thus, the spectrum produced by pair production will have three peaks, one corresponding to the energy of the initial gamma ray, one corresponding to the case where one of the 511 keV gamma rays is totally absorbed whilst the other passes directly out of the scintillator, which peak will have an energy 511 keV less than the first, and a third peak corresponding to the case where both 511 keV gamma rays pass out of the scintillator, which peak will be 1.022 MeV less than the first. Furthermore, there will be a high background level corresponding to the other reactions possible.

For any element in the coal, the neutrons will generate a spectrum of gamma rays having several lines. Each of these lines may generate a corresponding peak in the light from the detector, if they are less than 1.022 MeV, or three peaks if they are greater than that energy. If the peaks were very sharp (i.e. had a very low energy spread), it would be possible to analyse the light output from the scintillator and thereby generate the full spectrum of incident gamma rays, enabling the elements to be identified. However, in practice, each peak generated by the scintillator has an energy spread of about 7 to 10% of its value, so that if there are a large number of peaks, they tend to blend together. Furthermore, the background noise of one line in the incident gamma ray spectrum, may be greater than the maximum peak height for another line, so that lines may be completely lost within the background noise. The result is that the output from a single scintillator is impossible to analyse because all the peaks are blurred together.

The second type of detector used is a solid-state detector based on a single crystal of germanium (Ge). Again, an incident gamma ray may react by Compton scattering or by pair production, but instead of generating electrons which generate light as they move through the scintillator, the effect of interaction within a solid-state detector is to generate electron-hole pairs which move through the crystal as a current which may be detected by applying a voltage across the semiconductor. This current will have energy peaks corresponding to the energy peaks generated by the gamma ray interactions. The advantage of solid-state detectors is that they have very sharp peaks (with a spread often 0.1% or less of the energy of the peak, so that it would be possible to use the energy peaks from a solid-state detector to obtain a complete analysis of the gamma ray spectrum and hence of the elements present in the coal. However, the problem with solid-state detectors is that they have a low efficiency, in that they produce a much lower output than a scintillator for the same gamma ray flux. Therefore, a longer analysis time is needed when using a solid-state detector to obtain accurate results, and in practice, this time is far too long to permit continuous, or relatively short-term, analysis of the coal. Therefore, despite its high accuracy, a solid-state detector is unsuitable for analysis of coal in the way proposed by the present invention.

SUMMARY OF THE INVENTION

The present invention seeks to overcome the problem of multiplicity of lines and background noise of a scintillator detector, by providing a detector having a plurality of separate scintillators (referred to as a composite detector). The use of such a composite detector in prompt neutron activation analysis of coal is a first aspect of the present invention.

The composite detector detects primary events occurring in one of the scintillators, and simultaneously looks for secondary events in other scintillators. It then uses either coincidence or anti-coincidence of those events to eliminate many of the primary events from analysis, and it is found that this enables the background noise to be substantially eliminated, and also for particular peaks of the spectrum to be selectively detected.

Consider a primary Compton scattering event in one detector. If the gamma ray is totally absorbed, whether in one reaction or several, within that scintillator, then the light output is a measure of the gamma ray energy. If, however, a gamma ray emerges from the central scintillator and passes to another scintillator, it will generate a secondary event there. If this happens, the gamma ray event in the central scintillator is then ignored. The result is that the background noise level is substantially eliminated, and a full energy peak is selectively obtained. It is found that in this way a sufficiently accurate output can be obtained to enable the spectrum of the gamma rays to be determined.

Consider now a pair-production event. Again, if the gamma ray reacts entirely within one scintillator of the composite detector, the energy output corresponds to the gamma ray energy. If one of the 511 keV gamma rays is absorbed within the first scintillator, whilst the other passes to another scintillator, then that event could be ignored, so that the spectrum would consist entirely of the peak corresponding to the incident gamma ray. Alternatively, only such events could be selected in which case there is selection of the energy peak 511 keV less than the energy of the incident gamma ray. There is also the possibility that both 511 keV gamma rays escape from the first scintillator. Since they are in opposite directions, they will generate events in two other scintillators of the composite detector. Again, such events could be ignored, to enable the peak corresponding to the peak of the gamma ray to be selected.

However, it is also possible to make use of the fact that the two gamma rays from electron-positron annihilation travel in opposite directions to provide a detector which selectively detects events in which the two 511 keV gamma rays both pass out of the first scintillator. This idea is a second, independent, aspect of the present invention, and provides a gamma ray detector which may be used for analysis of gamma rays of any type (provided they have energies greater than 1.022 MeV), whether they are generated by neutron activation of coal or in any other way. This second aspect of the invention proposes an array of scintillators, which array extends in two dimensions substantially perpendicular to the direction of incidence of the gamma rays. The detector looks for events occurring in one of the scintillators, in which events simultaneously occur in the two adjacent, but opposite detectors. It should be noted here that the idea of "simultaneous" detection depends on the resolution of the detection equipment, but in practice will be of the order of 50 ns.

Where an event is detected in one scintillator, and also in the two adjacent but opposite scintillators, there is an extremely high probability that such an event is caused when an incident gamma ray reacts by pair production in the central scintillator and the two 511 keV gamma rays emerge from that central scintillator in opposite directions and are absorbed in the two adjacent scintillators. If the detector selectively detects such events, then the result is a peak of energy 1.022 MeV less than the energy of the incident gamma ray, and again, background noise is substantially eliminated.

Furthermore, since the detector consists of an array of scintillators, an event in any scintillator may be used as the "central" event, and events looked for in any two adjacent, but opposite scintillators to that central scintillator selected. In practice, this means that a very large number of events can be analysed, thereby increasing the efficiency of the detector.

When analysing coal, it is not necessary to use a single detector. In a third aspect of the present invention, two different detectors are used, or alternatively two detectors are used with different neutron sources, so that in either case the two detectors generate different spectra. Since the gamma rays come from the same coal sample, it is then possible to compare the results from the two detectors, and so get a more accurate analysis than is otherwise possible. For example, by suitable selection of the sources it is possible to arrange for one detector to detect elements of the coal including oxygen (which may be up to 20% of the total), whereas the second detector detects elements other than oxygen. In this way the first detector obtains an overall analysis of the coal while the second detector, because it is not detecting one of the major elements, enables more accurate analysis of the other elements present. By putting the two results together, a more complete analysis can be obtained. Furthermore, when two detectors are used it is possible to use two different methods for obtaining the same gamma ray energy lines, for example by using one composite detector utilizing anti-coincidence and another composite detector utilizing coincidence of a central event and two 511 keV gamma rays as described above. In this way, the two results may be compared. The present invention, insofar as it relates to coal analysis, can use any standard neutron source, although some sources are particularly useful, and can analyse the coal either continuously on a conveyor, or in batches on a hopper. In general it is advantageous to have the neutron source and detector(s) on opposite sides of the coal sample, although other geometries are possible. Whatever the method or geometry, the present invention permits accurate and rapid analysis of the elements present in the coal, so enabling the economic value of the coal to be determined.

BRIEF DESCRIPTION OF THE DRAWINGS

Embodiments of the invention will now be described in detail, by way of example, with reference to the accompanying drawings in which.

DETAILED DESCRIPTION

Figure 1:
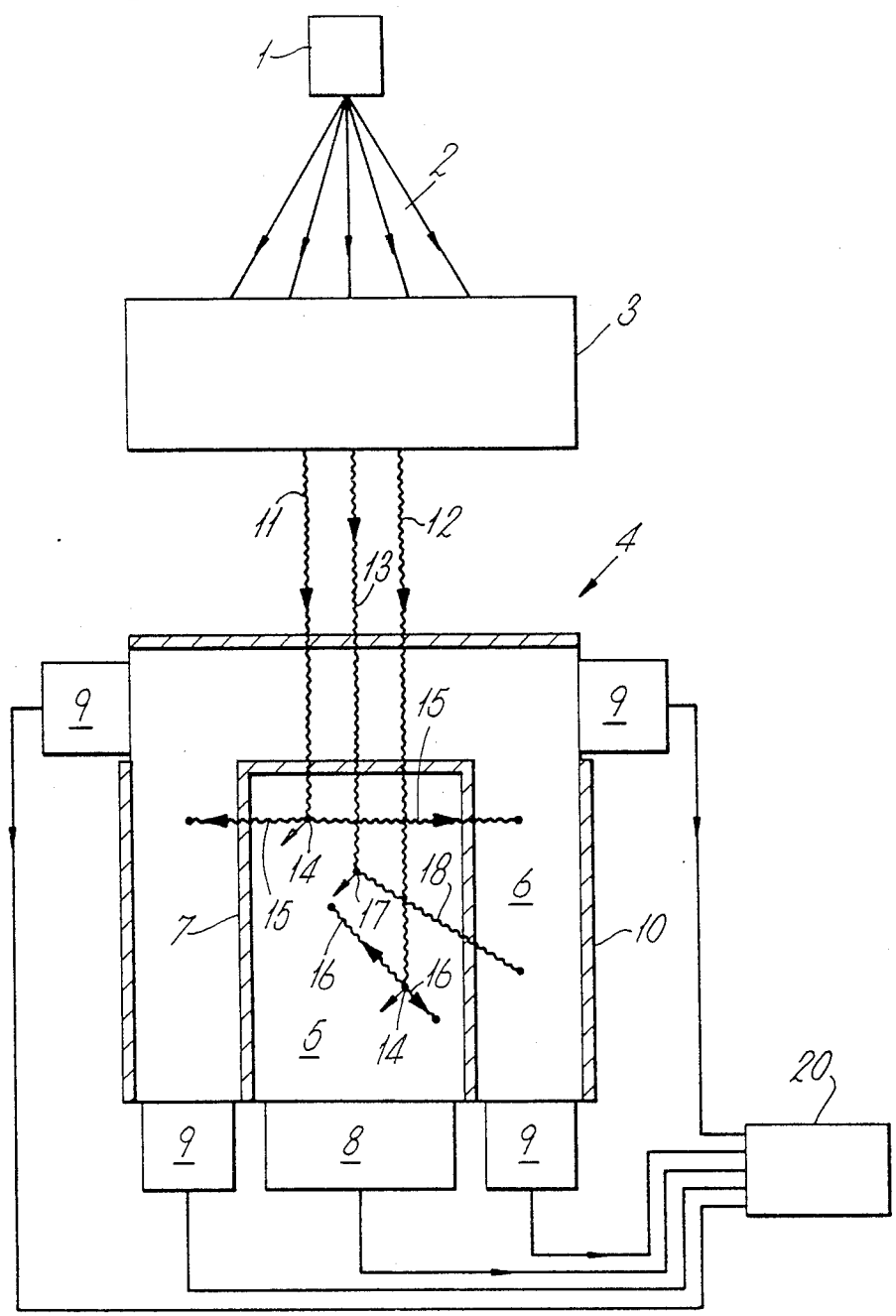
FIG. 1 shows a coal analysis system according to a first embodiment of the invention.

Referring first to FIG. 1 a neutron source 1 emits neutrons 2 which are incident on a sample of coal or other ore 3. The particular neutron source 1 used is not critical, and there are many known neutron sources which are suitable. Of particular applicability are neutron sources based on $^{241}$Am/Be which cause prompt neutron activation of a range of elements in the coal including oxygen, and $^{252}$Cf (which produces no significant prompt neutron activation of oxygen). The coal sample 3 may be a stationary mass of coal in a hopper, or a mass of coal moving continuously along a conveyor through the analysis system. The thickness of the coal sample 3 is also not critical, but is preferably within the range 10 to 50 cm, although about 25 cm is particularly advantageous. The neutrons 2 interact with atoms in the coal to generate gamma rays which are emitted in all directions. To optimise the useful gamma rays from the coal relative to the unwanted neutrons and gamma rays from the source and construction materials, it is preferable to use "transmission" geometry in which a gamma ray detector 4 is on the opposite side of the coal sample 3 to the neutron source 1.

The detector 4 illustrated in FIG. 1 comprises a central scintillator 5 of NaI(Tl) The central scintillator 5 is preferably a rectangular block of a sufficient size to ensure that the majority of gamma rays incident on it will be absorbed. The central scintillator 5 is surrounded on five of its six sides by an outer scintillator 6 (which may, in fact, be a number of separate scintillator blocks). The central scintillator 5 and the outer scintillator 6 are separated by a light reflective layer 7, so that light generated within the central scintillator 5 does not pass to the outer scintillator 6. A light detector 8, for example, a bank of photomultiplier tubes, is provided adjacent the sixth side of the central scintillator 5. This detects any light generated within the central scintillator, and generates an output which is fed to an analysis circuit 20. Similar light detectors 9 are provided at suitable positions around the outer scintillator 6, and the rest of the outer surface of the outer scintillator 6 is covered with a light reflective coating 10, similar to the light reflective layer 7, so that light generated within the outer scintillator 6, is passed to the light detectors 9. The output of the detectors 9 is also passed to the analysis circuit 20.

Consider now three gamma rays 11, 12 and 13 emitted by the coal sample 3 and incident on the detector 4. Assume that in each case their first interaction is within the central scintillator. As described above, there are many possible reactions, and FIG. 1 illustrates 3 of these. Gamma ray 11 has an energy greater than 1.022 MeV, and interacts with nuclei 14 in the central scintillator 5 to cause the generation of an electron-positron pair. The electron generates light which is detected by the light detector 8, whilst the pair of 511 keV gamma rays 15 both pass out of the central scintillator 5 and react by Compton scattering with electrons in the outer scintillator 6. These electrons generate light which is detected by the light detectors 9. This event therefore generates a simultaneous (within 50 ns) event in both the central scintillator 5 and in the outer scintillator 6 which can be detected by the analysis circuit 20. Gamma ray 12, on the other hand, similarly produces a pair of 511 keV gamma rays 16, but these interact only with electrons in the central scintillator 5. Therefore, this event causes light generation only in the central scintillator 5. A third possible reaction, illustrated by gamma ray 13, is where the gamma ray 13 reacts by Compton scattering with an electron 17 in the central scintillator 5, causing it to move through the lattice and so generate light. It is possible for all the energy of the gamma ray 13 to be absorbed in the central scintillator 5, in which case the light output to the light detector 8 is a direct measure of the energy of the gamma ray 13, but as illustrated, another gamma ray 18 is emitted which passes into the outer scintillator 6 to interact with an electron there, so generating light which is detected by light detectors 9.

Figure 2:
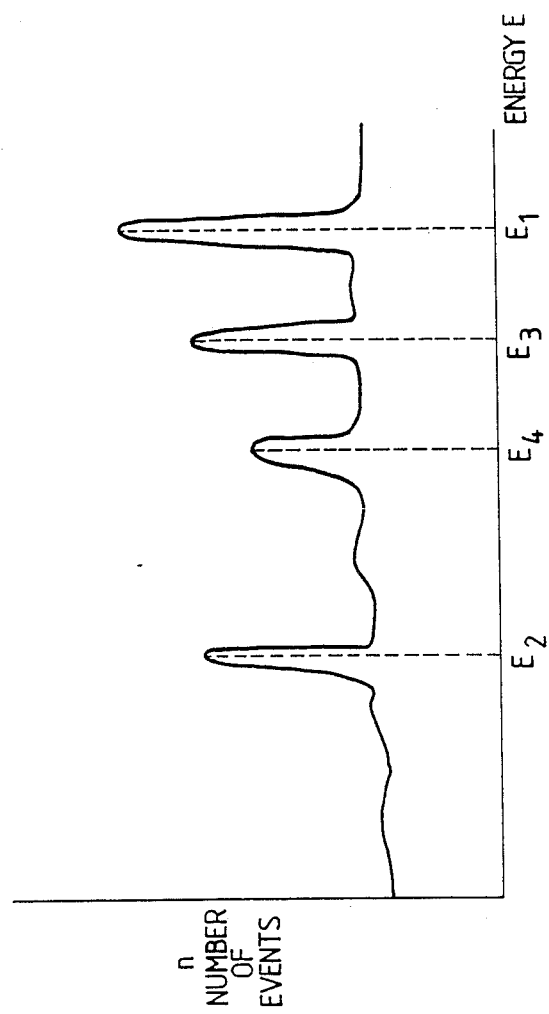
FIG. 2 shows an energy spectrum corresponding to the output of one scintillator of the detector of FIG. 1.

Consider now the output of the light detector 8 for the simplified case in which a particular element of the coal 3 has a gamma ray spectrum consisting only of a line with an energy $E_1$ greater than 1.022 MeV, and one line with an energy $E_2$ much less. The resultant output is shown in FIG. 2, in which the ordinate axis n, indicates the number of events detected, and the abscissa E represents the energy of the light of the event. As can be seen from FIG. 2, the output of the light detector 8 has a peak at energy $E_1$, and a second peak at energy $E_2$. These two peaks correspond to the case where all the energy of the gamma rays are absorbed within the central scintillator 5. There are, however, two other peaks. The first, at energy $E_3$ corresponds to the case where one of the gamma rays produced in a pair production event is absorbed within the central scintillator 5, and the other passes to the outer scintillator 6, resulting in light generation there. The second peak, at energy $E_4$ corresponds to the case where both gamma rays produced in a pair production event pass out of the central scintillator 5 to the outer scintillator 6. Thus, the difference in energy between peaks $E_1$ and $E_3$, and between peaks $E_3$ and $E_4$, is 511 keV. It can be seen that there is also a high background count corresponding to other possible interaction events.

When considering this simple case, the lines can be easily identified, but it must be remembered that in practice any element within the coal will have a gamma ray energy spectrum with a large number of lines, and furthermore that each element will have a different spectrum. Since the width of the lines is about 7%–10% of the energy of that line, it can be seen immediately that when the spectrum consists of more than a small number of lines they rapidly become blurred, particularly because some of them have only a low frequency over the background noise.

Therefore, the outputs of the light detectors 8 and 9 are passed to an analysis system which analyses those events which result in light generation in the central detector 5 only, i.e. where the light output is related directly to the energy of the gamma ray incident on the detector. Clearly, this will eliminate the peaks at energies $E_3$ and $E_4$, as they involve one or both gamma rays from pair production passing to the outer detector 6, but it is also found that it virtually eliminates the background noise, so that the result is that the peaks at energy $E_1$ and $E_2$ are selectively identified. It is found that even for the complex spectra generated by the elements present in a coal sample, it is possible with such a system to identify the elements accurately within a practicable working time, and by noting the height of the peaks measure their concentration.

Figure 3:
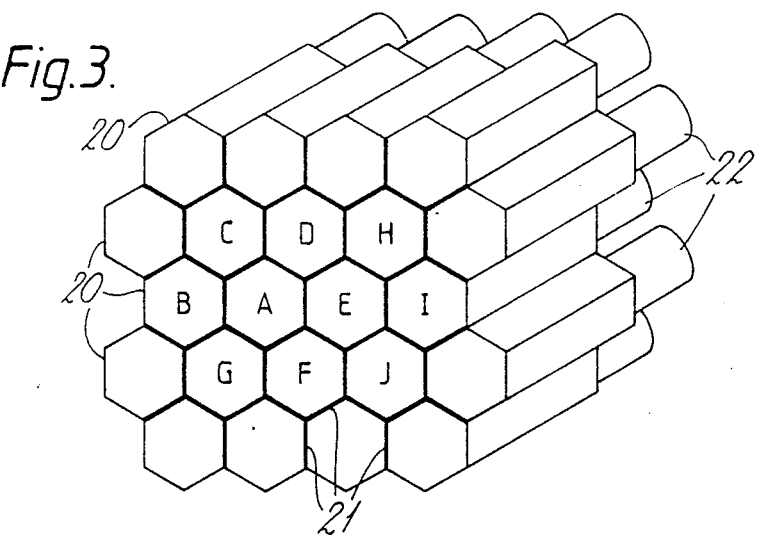
FIG. 3 shows a part of a detector being a second aspect of the present invention.

Another detector, which may be used instead of the detector 4 of FIG. 1, is shown in FIG. 3. This consists of an array of scintillators 20. As illustrated, the scintillators 20 have a hexagonal cross-section so that they can be fitted together with no gaps, but it would also be possible to use scintillators with circular or other cross-sections, but there may be gaps between the scintillators which would result in some loss of efficiency. As with the detector of FIG. 2, the adjacent surfaces of the scintillators 20 are provided with light reflective coatings 21 so that light generated within that scintillator does not pass to any of the others. One end of the array of scintillators is placed near the sample, and light detectors 22, such as photomultiplier tubes are provided at the other end of each scintillator 20. In that way, it is possible to detect an event in each scintillator 20.

Consider now a gamma ray of energy greater than 1.022 MeV which interacts by pair production in scintillator A of the array of FIG. 3. It will generate an output to its corresponding light detector 22, with the three peaks $E_1$, $E_3$, and $E_4$ of FIG. 2 (assuming the incident gamma ray has energy $E_1$). Again, with a complex spectrum, the results from any one scintillator would be impossible to analyse. However, energy peak $E_4$ corresponds to the case where both 511 keV gammas pass out of the scintillator A. Remembering that these two gamma rays are emitted in opposite directions, they will be detected either by the pair of scintillators B and E, or by the pair C and F, or by the pair D and G. Suppose now the outputs of all the scintillators A to G are investigated and events are detected in which there is light emission in scintillator A, and also in one of the pairs of scintillators BE, CF, and DG. This then selectively identifies the energy peak, $E_4$ (which is 1.022 MeV less than the energy of the incident gamma ray).

Figure 4:
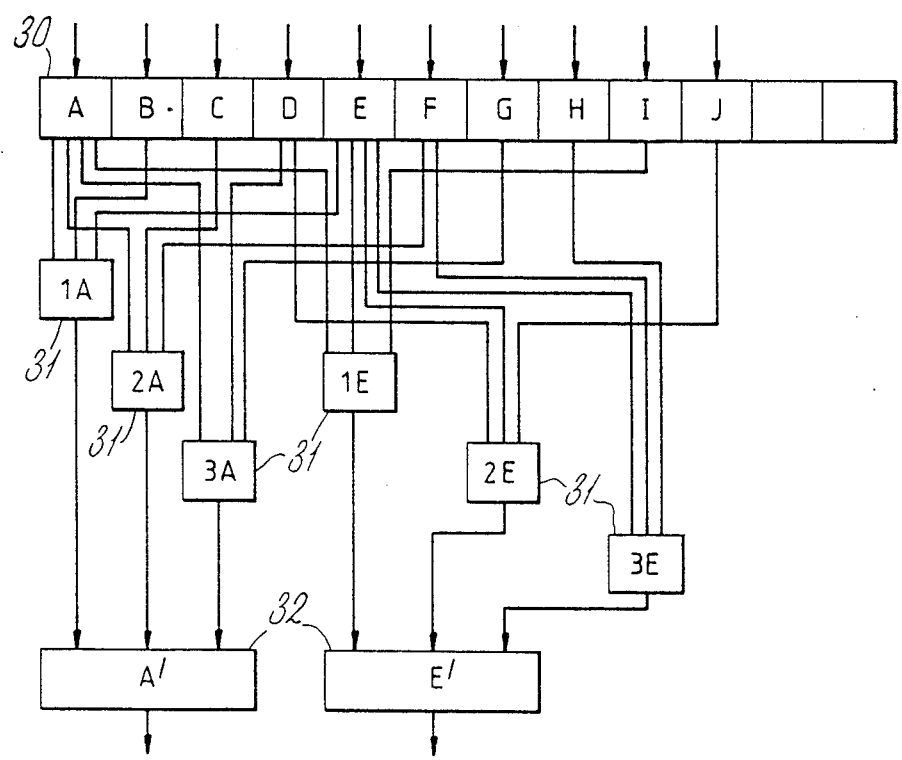
FIG. 4 shows part of the processing circuitry for the detector of FIG. 3.

Consider now the analysis system of FIG. 4 in which the signals from the light detectors 22 are transmitted to a register 30, and held for a period of about 50 ns. Connected to this register are AND gates 31 (only six being shown for convenience) and the AND gates 31 are connected in groups of three to OR gates 32. Suppose now that an event is detected in scintillator A, and simultaneously (within 50 ns) at detectors B and E. This corresponds to a gamma ray event in which the incident gamma generates an electron-positron pair, and the two 511 keV gamma rays pass to detectors B and E. Then, this event is detected by AND gate 1A which generates an output to OR gate 32. If the event only generates signals in scintillators A and B, there is no output. Similarly, AND gate 2A will detect an event occurring in scintillator A, and also in scintillator C and F, and AND gate 3A will generate an event in scintillator A and scintillators D and G. Thus, the outputs from the AND gates 1A, 2A, and 3A, correspond to the events in which the gamma ray interaction in scintillator A is simultaneous with events in the adjacent, but opposite pair of scintillators. Thus, the output of OR gate A' corresponds to any one of these events. The simultaneous analogue output of detector A has a spectrum consisting almost entirely of lines corresponding to pulses with an energy 1.022 MeV less than the energy of the incident gamma ray. Thus by accepting only those analogue pulses from detector A for which there is a logic signal A' the background noise is eliminated, and so results can be achieved.

However, it must be borne in mind that the detector of FIG. 3 has an array of scintillators, and therefore the analysis of events based on an event in detector A, is only one possible arrangement. The scintillator E can be similarly be used as the central scintillator, and the analysis can be based on an event in scintillator E, and also simultaneously in both of pairs of scintillators A and I, D and J, or H and F. Again, three AND gates 1E, 2E, 3E are used to detect these simultaneous events, and their outputs fed to OR gate E' whose output then corresponds to an identifiable pulse of the energy spectrum of the incident gamma rays. In practice, the detector is arranged so that the analysis system can use a light pulse in any one scintillator and look for simultaneous events in any two adjacent scintillators on opposite sides of the central one. It is this idea of a composite scintillator looking specifically for simultaneous events in three scintillators, that is an independent aspect of the present invention, because it can be used in other systems in addition to coal analysis. It is applicable wherever the energy of gamma rays (of energy greater than 1.022 MeV) needs to be investigated.

Furthermore, the coal analysis system may use two detectors, either identical or, for example, one similar to that shown in FIG. 1 and one similar to that shown in FIG. 3. In this way, the spectra of the gamma rays may be investigated in two different ways, and the results compared so that a more accurate result can be obtained. Furthermore, by using two different sources, it is possible to have one detector which is primarily investigating the amount of e.g. oxygen, and another which investigates the other elements, enabling those other elements to be analysed more precisely, without their peaks being swamped by the oxygen and carbon inelastic scattering lines.

As mentioned above, the system is applicable both to a continuous fed system and to a batch system.

I claim:

1. A gamma ray detector system comprising:
   a plurality of scintillators for detecting gamma rays as detection events and generating outputs corresponding to said detection events, said scintillators being arranged adjacent each other in an array;
   means for detecting one of said outputs from any of said scintillators, and for selecting the scintillator corresponding to that output as a primary scintillator;

means for selecting two other scintillators of said plurality of scintillators on opposite sides of said primary scintillator; and means for detecting outputs from said two other scintillators which are coincident with said one of said outputs from said primary scintillator.

2. A gamma ray detector system according to claim 1, wherein said array extends in a plane, and each of said plurality of scintillators are hexagonal in cross-section parallel to said plane.

3. A method of analyzing batches of a material which generates gamma rays when subjected to neutrons, said material being selected from the group consisting of coal and ore, said method comprising:

carrying out the following steps on a first batch of said material;

(a) passing the batch of said material between a source means and a detector;

(b) subjecting said material to neutrons from said source means so as to cause said material to generate said gamma rays;

(c) detecting by said detector said gamma rays generated by said material, sad detector having a plurality of scintillators arranged adjacent each other in an array, each of said scintillators generating a detection event on detection of one of said gamma rays, and generating an output corresponding to each said gamma ray detection event;

(d) for each said detection event, selecting the corresponding one of said plurality of scintillators as a primary scintillator;

(e) selecting two other scintillators from said plurality of scintillators, those two other scintillators being on opposite sides of said primary scintillator;

(f) for each said detection event, detecting if coincidence of said detection event in said primary scintillator is coincident with detection events in both said two other scintillators;

(g) analyzing the outputs of the selected primary detectors corresponding to said coincidence, so as to determine the composition of said first batch of material; and repeating steps (a) through (g) for further batches of said material.

4. A method according to claim 3, wherein said step (g) of analyzing the outputs comprises:

determining from said outputs the energies of the corresponding gamma rays.

5. A method of analyzing continuously a material which generates gamma rays when subjected to neutrons, said material being selected from the groups consisting of coal and ore, said method comprising:

(a) passing said material continuously between a source means and a detector;

(b) subjecting said material to neutrons from said source means so as to cause said material to generate said gamma rays;

(c) detecting by said detector said gamma rays generated by said material, said detector having a plurality of scintillators arranged adjacent each other in an array, each of said scintillators generating a detection event on detection of one of said gamma rays, and generating an output corresponding to each said gamma ray detection event;

(d) for each said detection event, selecting the corresponding one of said plurality of scintillators as a primary scintillator;

(e) selecting two other scintillators from said plurality of scintillators, those two other scintillators being on opposite sides of said primary scintillator;

(f) for each said detection event, detecting if coincidence of said detection event in said primary scintillator is coincident with detection events in both said two other scintillators, and;

(g) analyzing the outputs of the selected primary detectors corresponding to said coincidence, so as to determine continuously the composition of said material.

6. A method according to claim 5, wherein said step (g) of analyzing the outputs comprises:

determining from said outputs the energies of the corresponding gamma rays.

7. A method of analyzing a material which generates gamma rays when subjected to neutrons, said method comprising:

subjecting said material at a site to first neutrons from a first neutron source of first properties:

detecting first gamma rays generated from said material, when said material is subjected to said first neutrons, by prompt neutron activation substantially at the site at which said material is subjected to said first neutrons, so as to generate first gamma ray detection events corresponding to said first gamma rays detected, and generating first outputs corresponding to said first gamma ray detection events;

determining from said first outputs energies of the first gamma rays corresponding to said first outputs;

generating a first energy spectrum of the energies of the first gamma rays corresponding to said first outputs;

subjecting the material at a site to a second neutrons from a second neutron source of second properties;

detecting second gamma rays generated from said material when said material is subjected to said second neutrons, by prompt neutron activation substantially at the site at which said material is subjected to said second neutrons, so as to generate second gamma ray detection events corresponding to said second gamma rays detected, and generating second outputs corresponding to said second gamma ray detection events;

determining from said second outputs energies of the second gamma rays corresponding to the second outputs;

generating a second energy spectrum of the second gamma rays corresponding to said second outputs; and comparing said first and second energy spectra so as to determine the composition of said material.

8. A method as claimed in claim 7 wherein said material is subjected to said first neutrons and to said second neutrons at the same site.

9. An analysis system for analyzing a material which generates gamma rays when subjected to neutrons, said system comprising:

source means for subjecting said material to neutrons;

two detectors for detecting gamma rays when said material is subjected to said neutrons and generating a gamma ray detection event on detection of one of said gamma rays, each of said two detectors including generating means for generating an output corresponding to each said gamma ray detection event, said two detectors having different gamma ray detection properties;

each of said two detectors comprising a plurality of scintillators, said generating means including means associated with each scintillator for generating gamma ray detection events in each scintillator;

said generating means of one of said two detectors including means for generating an output in dependence on anticoincidence of gamma ray detection events in any two of the scintillators of said one detector; and said generating means of the other of said two detectors includes means for generating output in dependence on coincidence of gamma ray detecting events on any three adjacent scintillators of said other detector; and means for analyzing said outputs of said generating means;

wherein said two detectors cause said analyzing means to generate two sets of results respectively corresponding to the effect of the different detection properties of said two detectors, and said analyzing means includes means for comparing said two sets of results to analyze said material.

* * * * *